(12) United States Patent
Plochocka

(10) Patent No.: US 6,214,956 B1
(45) Date of Patent: Apr. 10, 2001

(54) SOLVENT-FREE COPOLYMERS OF MALEIC ANHYDRIDE AND ALKYL VINYL ETHERS HAVING A SPECIFIC VISCOSITY OF 0.5 TO 5 AND METHOD OF MAKING

(75) Inventor: Krystyna Plochocka, Scotch Plains, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/268,834

(22) Filed: Mar. 16, 1999

Related U.S. Application Data

(63) Continuation of application No. 08/942,830, filed on Oct. 2, 1997, now Pat. No. 5,939,506.

(51) Int. Cl.$^7$ ............................ C08F 224/04; C08F 34/02
(52) U.S. Cl. ............................ 526/272; 526/271; 526/64; 528/497
(58) Field of Search .................................. 526/272, 271, 526/64; 528/497

(56) References Cited

U.S. PATENT DOCUMENTS

| | | | |
|---|---|---|---|
| 3,868,432 | * 2/1975 | Keegan et al. | 260/874 |
| 4,435,536 | * 3/1984 | Kato et al. | 524/378 |
| 4,627,977 | * 12/1986 | Gaffar et al. | 424/52 |
| 4,721,761 | * 1/1988 | Omae et al. | 526/64 |
| 4,962,185 | * 10/1990 | Tazi et al. | 528/497 |
| 5,047,490 | * 9/1991 | Pehlah et al. | 526/271 |
| 5,066,481 | * 11/1991 | Helioff et al. | 424/47 |
| 5,147,963 | * 9/1992 | PLochocka | 526/332 |
| 5,166,271 | * 11/1992 | Masuko et al. | 525/282 |
| 5,214,089 | * 5/1993 | Login et al. | 524/418 |

\* cited by examiner

*Primary Examiner*—David W. Wu
*Assistant Examiner*—Tanya Zalukawa
(74) *Attorney, Agent, or Firm*—Walter Katz; William J. Davis; Marilyn J. Maue

(57) ABSTRACT

Solvent-free, free-flowing, fine white powders of a copolymer of maleic anhydride and a $C_1$–$C_4$ alkyl vinyl ether having a specific viscosity of about 0.5 to about 5 (1% wt/v in methyl ethyl ketone, 25° C.) and substantially without residue, odor or taste. A solvent-free process of polymerizing the monomers in the presence of 0.01 to 1.9% acetaldehyde also is described.

3 Claims, 1 Drawing Sheet

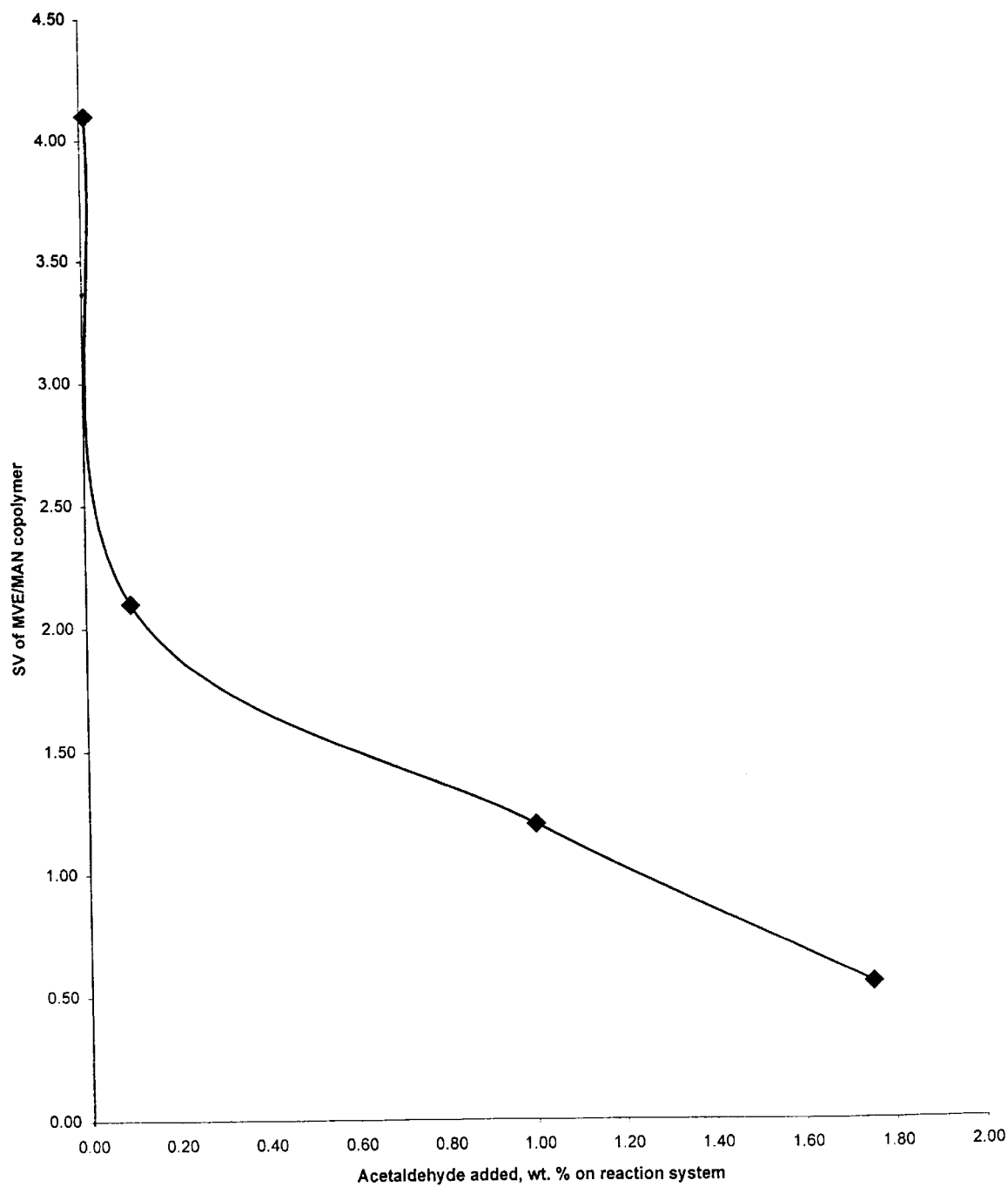

SOLVENT-FREE COPOLYMERS OF MALEIC ANHYDRIDE AND ALKYL VINYL ETHERS HAVING A SPECIFIC VISCOSITY OF 0.5 TO 5 AND METHOD OF MAKING

CROSS-REFERENCE TO RELATED PATENT APPLICATIONS

This application is a continuation of U.S. patent application Ser. No. 08/942,830, filed Oct. 2, 1997, now U.S. Pat. No. 5,939,506.

BACKGROUND OF THE INVENTION

1. Field of the Invention

This invention relates to a process for making a copolymer of maleic anhydride and a $C_1$–$C_4$ alkyl vinyl ether, and, more particularly, to a solvent-free process for making such copolymer product in the form of free-flowing, fine white powders having a predetermined, substantially reduced specific viscosity, SV which is characterized by addition of a small amount of an active chain transfer agent to the reaction mixture, which agent can be easily volatilized without leaving substantially any residue, odor or taste in the product.

2. Description of the Prior Art

M. Tazi et al, in U.S. Pat. No. 5,003,014, described a process for making copolymers of maleic anhydride and a $C_1$–$C_4$ alkyl vinyl ether having specific viscosities extending over a wide range by addition of large, solvent quantities of toluene as chain transfer agent in the polymerization. However, toluene is a relatively inactive chain transfer agent for this polymerization. Accordingly, such solvent amounts of toluene were required to effect any reduction in the specific viscosity of the copolymer product. Furthermore, toluene was difficult to remove during the process steps of venting of excess alkyl vinyl ether and drying of the polymer, resulting in a toluene residue in the product, and some objectionable odor and taste.

Shimizu, H., in Jap. Kokai pat. Appln. No. Hei 6 [1994]-569; published Mar. 1, 1994, described a process of making very low molecular weight copolymers of maleic anhydride and alkyl vinyl ethers by including large amounts of higher alkyl aldehydes as a solvent in the system. Such aldehydes, however, are non-volatile and remain in the product giving it a particularly unpleasant odor.

Accordingly, it is an object of the present invention to provide a solvent-free process for making copolymers of maleic anhydride and a $C_1$–$C_4$ alkyl vinyl ether in the presence of an active chain transfer agent which can be included in small amounts in the polymerization mixture to effect a substantial reduction in the specific viscosity of the copolymer product, and which can be easily volatilized during removal of excess alkyl vinyl ether without degrading the copolymer and without leaving substantially any residue, odor or taste in the product.

A specific object is to provide copolymers of maleic anhydride and methyl vinyl ether which have a specific viscosity SV of about 0.5 to 5, preferably 1.0 to 4, by including about 0.01 to 1.9%, preferably 0.02 to 1.0, by weight of the reaction mixture, of acetaldehyde therein.

IN THE DRAWING

The FIGURE is a plot of SV of copolymer product vs. concentration of acetaldehyde added to the reaction mixture.

SUMMARY OF THE INVENTION

What is described herein is a solvent-free, free-flowing, fine white powder copolymer of maleic anhydride and a $C_1$–$C_4$ alkyl vinyl ether having a predetermined specific viscosity of about 0.5 to about 5, preferably 1.0 to 4, as measured on a 1% wt/vol solution of copolymer in methyl ethyl ketone at 25° C., a product substantially without residue, odor or taste.

As another feature of the invention, a solvent-free process is described for making such a copolymer product of maleic anhydride and a $C_1$–$C_4$ alkyl vinyl ether by copolymerizing maleic anhydride and excess alkyl vinyl ether with a radical initiator, stripping off excess alkyl vinyl ether, followed by drying the polymer at 40–100° C. under vacuum to remove any traces of remaining alkyl vinyl ether, wherein acetaldehyde is added to the reaction mixture as an active chain transfer agent in a predetermined amount of about 2% or less by weight, preferably 0.01 to 2%, and, most preferably 0.02 to 1.0%, thereby producing a copolymer product having a predetermined, substantially reduced specific viscosity, whose value is determined directly in relation to the amount of acetaldehyde added. The acetaldehyde is particularly characterized by its easy volatilization during removal of excess alkyl vinyl ether, without degrading the copolymer or leaving substantially any residue, odor or taste in the product.

The solvent-free process here is preferably embodied when the amount of acetaldehyde is about 0.01 to 1.9%, most preferably 0.02 to 1.0, whereupon the specific viscosity of the copolymer is about 0.5 to 5, preferably 1 to 4, as measured on a solution of copolymer of 1% wt/v in methyl ethyl ketone (MEK) at 25° C.

DETAILED DESCRIPTION OF THE INVENTION

The solvent-free polymerization process of the invention is carried out using an excess of alkyl vinyl ether as the reaction medium, characterized by precharging the alkyl vinyl ether into the reactor, adding a predetermined amount of acetaldehyde, adding a radical initiator, heating to a reaction temperature of about 50° to 100° C., and, thereafter, feeding molten maleic anhydride into the reactor over a predetermined period of time, followed by holding the reactants at a defined temperature for a predetermined period of time.

The remaining AVE is stripped off, the polymer is dried at about 40–100° C. under vacuum, to remove any remaining traces of AVE. The desired copolymer is obtained as a solvent-free, fine powder, of predetermined SV, which is odorless and tasteless.

In a preferred embodiment of the invention, the amount of acetaldehyde added is less than 2% by weight of the reaction mixture, preferably 0.01% to 2%, and optimally 0.02% to 1%. The MAN reactant preferably is introduced into the precharged MVE over a period of at least 1 hour and the % solids during the polymerization is about 10–40%. The MVE:MAN mole ratio is about 25:1 to 5:1, most preferably 12:1 to 7:1. The initiator concentration is 0.01 to 0.2%, most preferably 0.05 to 0.1% by wt., based on the copolymer obtained.

The invention will now be described in more detail with reference to the following examples.

EXAMPLE 1

A 1-liter Buchi pressure reactor was sparged with nitrogen and charged with 400 ml (300 g, 5.16 mol) of methyl vinyl ether (MVE), 0.55 g Trigonox® 21 (t-butylperoxy-2-ethylhexanoate, an initiator made by Akzo Nobel Chemicalls, Inc.), a concentration of 0.08% by weight based on copolymer obtained, and with 0.034 g of acetaldehyde, or 0.01% by weight based on total weight of the reaction system. The precharged reactor was heated to 75° C., with agitation, over 15 min. Then 41 g (0.418 mol) of molten maleic anhydride (MAN), was fed in over 1 hour, resulting in a MVE/MAN mole ratio of 12.3. The solids content of the resulting mixture was 16%. The temperature of 75° C. was maintained for 1.5 hours. Then excess MVE was stripped off, whereupon the pressure dropped to atmospheric. Upon opening the reactor, a fine, free-flowing copolymer powder was observed. The product was dried in a vacuum oven at 65° C. for 4 hours. A total of 64.8 g (99.37 % of theoretical yield) of product was obtained. $^{13}$C NMR analysis the product indicated a 1:1 MVE/MAN copolymer having a specific viscosity (SV) of 4.1 (1% w/v polymer solution in MEK at 25° C.). The product was odorless and tasteless (2.5% aqueous solution, pH 7).

EXAMPLES 2–4

Examples 24 were carried out as in Example 1, using different amounts of acetaldehyde.

The results of Examples 1–4 are summarized in the Table below:

TABLE

| Example No. | 1 | 2 | 3 | 4 |
|---|---|---|---|---|
| Acetaldehyde added, g | 0.034 | 0.34 | 3.4 | 6 |
| Acetaldehyde added, % on reaction blend | 0.01 | 0.1 | 1.0 | 1.75 |
| Specific viscosity of copolymer (SV, 1% wt/v in MEK), after drying | 4.1 | 2.1 | 1.2 | 0.55 |
| Appearance of copolymer | Solvent-free, fine white powders, without odor and taste | | | |

The attached FIGURE shows the effect of acetaldehyde addition to this polymerization mixture in accordance with the data in Examples 1–4. What is plotted is SV of copolymer vs. % acetaldehyde added. The results show a substantial reduction in SV with an increase in acetaldehyde added.

While the invention has been described with particular reference to certain embodiments thereof, it will be understood that changes and modifications may be made which are within the skill of the art. Accordingly, it is intended to be bound only by the following claims, in which:

What is claimed is:

1. A solvent-free process for making solvent-free, free-flowing, fine white powders of a copolymer product of maleic anhydride (MAN) and a $C_1$–$C_4$ alkyl vinyl ether (AVE) having a specific viscosity of about 0.5 to about 2 (1% wt/v in methyl ethyl ketone, 25° C.) and substantially without residue, odor or taste which comprises precharging a reactor with excess AVE, acetaldehyde as chain transfer agent and 0.01 to 0.2% based upon said product of a free radical initiator, feeding MAN into said precharged reactor over a period of at least 1 hour, said excess AVE being maintained at a mole ratio of AVE:MAN of 12:1 to 7:1, said acetaldehyde being present in said reaction mixture in a predetermined amount of 0.01 to 2% by weight thereof, copolymerizing said monomers at 55–80° C., stripping off excess AVE and drying under vacuum at 40–100° C. to remove any remaining traces of AVE, wherein when said amount of acetaldehyde is 1.75%, said specific viscosity is 0.55. and when said amount of acetaldehyde is 1.0%, said specific viscosity is 1.2.

2. A solvent-free process according to claim 1 wherein said alkyl vinyl ether is methyl vinyl ether.

3. A solvent-free process according to claim 1 in which drying is carried out at 40° to 100° C. under vacuum.

* * * * *